(12) United States Patent
Nishiyama et al.

(10) Patent No.: US 10,912,510 B2
(45) Date of Patent: Feb. 9, 2021

(54) INDEX DERIVING DEVICE, WEARABLE DEVICE, AND MOBILE DEVICE

(71) Applicants: THE UNIVERSITY OF TOKYO, Tokyo (JP); Rohm Co., Ltd., Kyoto (JP)

(72) Inventors: Hideki Nishiyama, Kyoto (JP); Tadashi Kobayashi, Kyoto (JP); Atsushi Momota, Kyoto (JP); Masafumi Seike, Kyoto (JP); Senshi Fukashiro, Tokyo (JP)

(73) Assignees: Rohm Co., Ltd., Kyoto (JP); The University of Tokyo, Tokyo (JP)

( * ) Notice: Subject to any disclaimer, the term of this patent is extended or adjusted under 35 U.S.C. 154(b) by 239 days.

(21) Appl. No.: 15/577,496

(22) PCT Filed: May 31, 2016

(86) PCT No.: PCT/JP2016/066047
§ 371 (c)(1),
(2) Date: Nov. 28, 2017

(87) PCT Pub. No.: WO2016/194907
PCT Pub. Date: Dec. 8, 2016

(65) Prior Publication Data
US 2018/0146907 A1    May 31, 2018

(30) Foreign Application Priority Data
Jun. 5, 2015  (JP) .................................. 2015-114839

(51) Int. Cl.
*A61B 5/22*    (2006.01)
*A61B 5/00*    (2006.01)
(Continued)

(52) U.S. Cl.
CPC ............ *A61B 5/224* (2013.01); *A61B 5/0002* (2013.01); *A61B 5/1118* (2013.01);
(Continued)

(58) Field of Classification Search
CPC ........... A61B 5/224; A61B 5/227; A61B 5/22; A61B 5/221; A61B 5/0002; A61B 5/1118;
(Continued)

(56) References Cited

U.S. PATENT DOCUMENTS 6,183,365 B1    2/2001  Tonomura et al.
2001/0053883 A1*  12/2001  Yoshimura ........... A61B 5/0537
                                                        600/587
(Continued)

FOREIGN PATENT DOCUMENTS

EP         0842436       5/1998
JP         H09-325081    12/1997
(Continued)

OTHER PUBLICATIONS

Henwood, Tim et al. "Strength Versus Muscle Power-Specific Resistance Training in Community-Dwelling Older Adults", Journal of Gerontology: Medical Sciences 2008, vol. 63A, No. 1, 83-91 (Year: 2008).*
(Continued)

*Primary Examiner* — Matthew Kremer
*Assistant Examiner* — Avery M Foley
(74) *Attorney, Agent, or Firm* — Fish & Richardson P.C.

(57) ABSTRACT

A subject performs a sit-to-stand operation while wearing a device (SU) that contains an acceleration sensor (11) on the front of the chest. The present invention derives a muscular strength index representing the muscular strength of a human body by obtaining maximum acceleration value data from a signal expressing the size of an acceleration vector comprising a tri-axial component in detected acceleration,
(Continued)

and using the maximum acceleration value data and the muscle mass or body fat mass of the subject. The present invention has the ability to derive a physical activity amount from the acceleration detection results, and on the basis of the activity amount (ACT) during a prescribed activity target period and the muscular strength index at the start and end times of the activity target period, obtains an activity efficiency index that corresponds to changes in the muscular strength index in response to the amount of activity.

10 Claims, 8 Drawing Sheets

(51) Int. Cl.
  A63B 71/06 (2006.01)
  A61B 5/11 (2006.01)
  A63B 24/00 (2006.01)
(52) U.S. Cl.
  CPC ............ *A61B 5/4884* (2013.01); *A61B 5/681* (2013.01); *A61B 5/7203* (2013.01); *A61B 5/7278* (2013.01); *A63B 24/0075* (2013.01); *A63B 71/06* (2013.01); *A63B 71/0622* (2013.01); *A61B 5/6823* (2013.01); *A61B 5/6824* (2013.01); *A61B 2560/0257* (2013.01); *A61B 2562/0219* (2013.01)
(58) Field of Classification Search
  CPC ... A61B 5/1124; A61B 5/1121; A61B 5/4884; A61B 5/4887; A61B 5/68; A61B 5/6801; A61B 5/6802; A61B 5/6806; A61B 5/681; A61B 5/72; A61B 5/7203; A61B 5/7207; A61B 5/7271; A61B 5/6823; A61B 5/6824; A61B 2560/0257; A61B 2562/0219; A63B 24/0062; A63B 24/0075; A63B 2024/0065; A63B 2024/0068; A63B 2024/001; A63B 2024/0078; A63B 2024/0081; A63B 2024/0093; A63B 71/06; A63B 71/0622
  See application file for complete search history.

(56) References Cited

U.S. PATENT DOCUMENTS

| 2004/0236246 | A1 | 11/2004 | Aoyagi et al. | |
|---|---|---|---|---|
| 2006/0191335 | A1 | 8/2006 | Nose et al. | |
| 2010/0211349 | A1* | 8/2010 | Flaction | A61B 5/1107 702/141 |
| 2011/0251495 | A1* | 10/2011 | Province | A61B 5/4866 600/483 |
| 2015/0305656 | A1* | 10/2015 | Takehara | A61B 5/1116 600/595 |
| 2017/0011210 | A1* | 1/2017 | Cheong | A61B 5/0022 |

FOREIGN PATENT DOCUMENTS

| JP | 2006-263449 | 10/2006 |
|---|---|---|
| JP | 2006-320533 | 11/2006 |
| JP | 2009-125506 | 6/2009 |
| JP | 2012-223452 | 11/2012 |
| JP | 2013-172757 | 9/2013 |
| JP | 2014061084 | 4/2014 |

OTHER PUBLICATIONS

Easthope, Christopher "Effects of a trail running competition on muscular performance and efficiency in well-trained young and master athletes.", Eur J Appl Physiol (2010) 110:1107-1116 (Year: 2010).*
Japanese Patent Office, International Search Report for PCT/JP2016/066047, dated Aug. 23, 2016 (with English Translation).
Shinsuke Yoshioka, et al, "Computation of kinematics and the minimum peak joint moments of sit-to-stand movements", BioMedical Engineering Online (2007).
Misfit Wearables, "Misfit Shine", online at "misfit.com/products/shine?locale=ja," 6 pages (2015).
European Patent Office; Extended European Search Report mailed in counterpart patent application No. 16803341.3 (dated Jan. 15, 2019).
Janssen W G M et al., "Analysis and Decomposition of Accelerometric Signals of Trunk and Thigh Obtained During the Sit-to-Stand Movement," Medical & Biological Engineering & Computing, Apr. 1, 2005 43:2:265-272.
M.M. Gross et al., "Effect of Muscle Strength and Movement Speed on the Biomechanics of Rising From a Chair in Healthy Elderly and Young Women," Gait & Posture, Dec. 1, 1998 8:3:175-185.
Juan J Gonz Lez-Badillo et al., "Moderate Resistance Training Volume Produces More Favorable Strength Gains Than High or Low Volumes During a Short-Term Training Cycle," Journal of Strength and Conditioning Research National Strength & Conditioning Association, Jan. 1, 2019, p. 689-697.

* cited by examiner

INDEX DERIVING DEVICE, WEARABLE DEVICE, AND MOBILE DEVICE

TECHNICAL FIELD

The present invention relates to index deriving devices, wearable devices, and mobile devices.

BACKGROUND ART

There have been proposed various techniques for measuring the amount of activity in a physical activity of a subject (see, for example, Patent Document 1 identified below).

As a movement for estimating the physical strength of a subject, an STS (sit-to-stand) movement is known which is also called a stand-up-from-a-chair movement. An STS movement is a movement that involves moving the center of gravity of the subject's body weight from a comparatively low support base face to a comparatively high position. In Non-Patent Document 1 identified below, a summary is presented of the relationship among the moments at the hip, knee, and ankle in an STS movement, and it is reported that, irrespective of how the subject stands up in an STS movement, the sum of the moments at the hip and knee in healthy subjects exhibits a constant value (1.53 N·m/kg) and that there is almost no correlation between that sum and the moment at the ankle. It is also reported that, if the sum of the moments at the hip and knee in an STS movement is less than the above-mentioned constant value, a problem is suspected in the subject's ability to stand up, suggesting the necessity for an appropriate exercise therapy to prevent confinement to bed and to motivate to rehabilitation. Incidentally, according to the method described in Non-Patent Document 1, reflective markers are placed on the subject's hip and knee respectively, the movement of those parts with the reflective markers in an STS movement is monitored with a high-sensitivity camera, and the moments that acts are derived according to equations of motion.

On the other hand, Non-Patent Document 2 identified below discloses a coin-type unit and a wearable device that are provided with a three-axis acceleration sensor and that can measure the number of steps and consumed energy in calories.

LIST OF CITATIONS

Patent Literature

Patent Document 1: Japanese Patent Application published as No. 2013-172757

Non-Patent Literature

Non-Patent Document 1: Shinsuke Yoshioka et al., Computation of kinematics and the minimum peak joint moments of sit-to-stand movements, BioMedical Engineering OnLine, 2007, 6:26, pp. 1-14 (accessible at the URL <http://www.biomedical-engineering-online.com/content/6/1/26>)

Non-Patent Document 2: Misfit Wearables, Misfit Shine, online, accessed on May 18, 2015 on the Internet, at the URL <http://misfit.com/products/shine?locale=ja>

SUMMARY OF THE INVENTION

Technical Problem

Although various techniques for measuring the amount of activity in a physical activity have been proposed, no devices have ever been proposed that can evaluate how a physical activity requiring a certain amount of activity improves body strength (such as muscular power), that is, so to speak, the quality of the physical activity.

Against such backgrounds, the present invention aims to provide an index deriving device, a wearable device, and a mobile device that can evaluate a change in physical strength brought about by a physical activity.

Means for Solving the Problem

According to one aspect of the present invention, an index deriving device which includes an acceleration sensor for sensing acceleration and which can derive the amount of activity of a human body includes: a muscular power index deriver configured to derive a muscular power index as to the muscular power of the human body based on the sensing result from the acceleration sensor; and a separate index deriver configured to derive a separate index commensurate with the variation of the muscular power index against the amount of activity during a predetermined activity monitoring period.

Specifically, for example, the separate index deriver can derive the separate index based on: the amount of activity derived based on the sensing result from the acceleration sensor during the activity monitoring period; the muscular power index derived based on the sensing result from the acceleration sensor during a first period relative to the start time point of the activity monitoring period; and the muscular power index derived based on the sensing result from the acceleration sensor during a second period relative to the end time point of the activity monitoring period.

For another example, the muscular power index deriver can derive the muscular power index based on an acceleration signal based on the sensing result from the acceleration sensor during an evaluation period in which the human body performs a predetermined movement.

In that case, for example, the muscular power index deriver can derive the muscular power index by using acceleration maximum value data contained in the acceleration signal.

More specifically, for example, the muscular power index deriver can derive the muscular power index by using: the acceleration maximum value data, the body weight of the human body, and the body fat percentage of the human body; or the acceleration maximum value data, the body weight of the human body, and the body fat mass of the human body.

For another example, the muscular power index deriver can derive the muscular power index by using: the acceleration maximum value data, the body weight of the human body, and the muscle percentage of the human body; or the acceleration maximum value data and the muscle mass of the human body.

Then, for example, the muscular power index deriver can derive, as the muscular power index, the acceleration maximum value per unit amount of muscle of the human body in the predetermined movement.

For another example, assuming that the acceleration sensed by the acceleration sensor contains an acceleration component due to the movement of the human body and an acceleration component due to gravity, the muscular power index deriver can derive the muscular power index by using the value obtained by subtracting the acceleration component due to gravity from the acceleration maximum value data.

For another example, the acceleration sensor can sense the acceleration along three mutually perpendicular axes individually, and the acceleration signal used to derive the muscular power index can represent the magnitude of the acceleration vector formed by the acceleration along the three axes.

For another example, the predetermined movement can include a movement in which the human body stands up.

For another example, there can be further provided an atmospheric pressure sensor for sensing the atmospheric pressure, and the amount of activity can be derived based on the sensing result from the acceleration sensor and the sensing result from the atmospheric pressure sensor.

For another example, the index deriving device can include: a circuit board which has mounted thereon: a sensor arrangement including the acceleration sensor, a calculation processor configured to derive the amount of activity and constituting the muscular power index deriver and the separate index deriver, and a wireless processor configured to conduct wireless communication; and a housing which houses the circuit board.

According to another aspect of the present invention, a wearable device includes an index deriving device as described above.

According to yet another aspect of the present invention, a mobile device includes an index deriving device as described above.

Advantageous Effects of the Invention

According to the present invention, it is possible to provide an index deriving device, a wearable device, and a mobile device that can evaluate a change in physical strength brought about by a physical activity.

DESCRIPTION OF EMBODIMENTS

Figure 1:
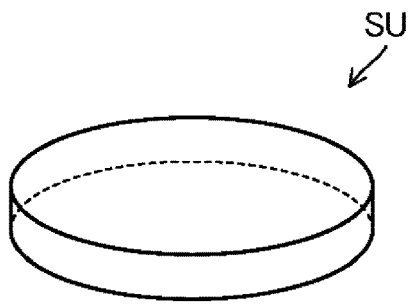
FIG. 1 is an exterior perspective view of a sensor unit, for use in a measurement device, according to a first embodiment of the present invention.

Embodiments of the present invention will be described specifically below with reference to the accompanying drawings. Among the drawings referred to in the course, the same parts are identified by the same reference numerals, and in principle no overlapping description as to the same parts will be repeated. In the present description, for the sake of simple description, symbols and other designations referring to information, signals, physical quantities, components, and the like are occasionally used with the names of the corresponding information, signals, physical quantities, components, and the like omitted or abbreviated.

First Embodiment

Figure 2:
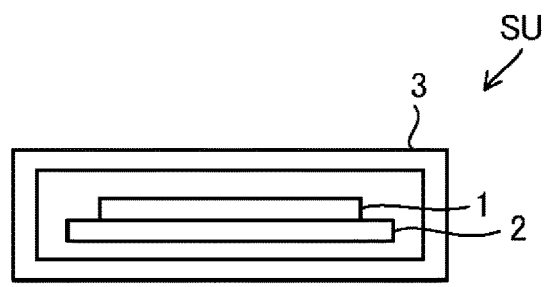
FIG. 2 is a diagram showing a structure of the sensor unit.

A first embodiment of the present invention will be described. FIG. 1 is an exterior perspective view of a sensor unit SU according to the first embodiment of the present invention. FIG. 2 is a schematic diagram showing the structure inside a housing 3 of the sensor unit SU. The sensor unit SU includes a component group 1, a circuit board 2, and a housing 3. On the circuit board 2, there are mounted electronic components that constitute the component group 1. The circuit board 2 having the component group 1 mounted on it is housed in and fastened to the housing 3, which is made of resin or metal and has a predetermined shape. The housing 3 has a cylindrical shape with a comparatively small thickness, so that the sensor unit SU has a shape like a medal; thus, the sensor unit SU can also be called a sensor medal. The housing 3 does not necessarily need to have a precisely cylindrical exterior shape; for example, a part corresponding to a base of the cylinder may be curved. The housing 3 may have any other exterior shape than cylindrical; for example, it may have the shape of a rectangular parallelepiped.

Figure 3:
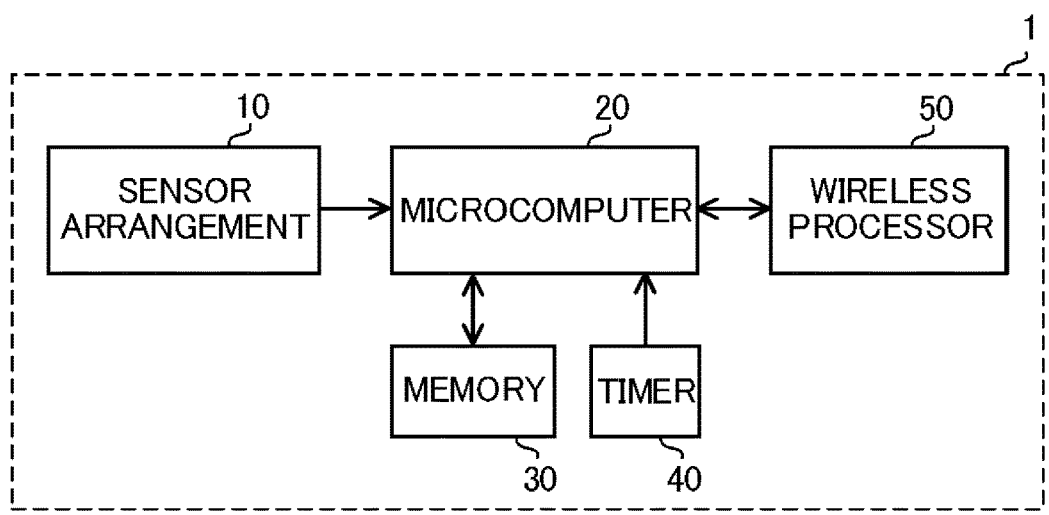
FIG. 3 is a block diagram of a component group in the sensor unit.

FIG. 3 is a configuration block diagram of the component group 1. The component group 1 includes a sensor arrangement 10, a microcomputer 20, a memory 30, a timer 40, and a wireless processor 50. The microcomputer 20 can be formed as a semiconductor integrated circuit. Or, the microcomputer 20, the memory 30, the timer 40, and the wireless processor 50 can be formed as a single semiconductor integrated circuit. In addition to the components constituting the sensor arrangement 10, the microcomputer 20, the memory 30, the timer 40, and the wireless processor 50, various components can be mounted on the circuit board 2 and housed in the housing 3. Though not expressly illustrated, a power supply circuit for supplying a supply voltage for driving, for example, the sensor arrangement 10, the microcomputer 20, the memory 30, the timer 40, and the wireless processor 50 may be mounted on the circuit board 2, and a battery (such as a lithium-ion battery) for supplying electric power to the power supply circuit may be housed in the housing 3.

The sensor arrangement 10 includes a sensor that senses a predetermined physical quantity or the like, and a signal representing its sensing results is fed from the sensor arrangement 10 to the microcomputer 20. The microcomputer 20, which constitutes an calculation processor, performs predetermined calculations (which will be described specifically later) based on the signal from the sensor arrangement 10, and also controls the operation of the sensor unit SU in a comprehensive manner. The memory 30 stores any information handled by the microcomputer 20. The timer 40 has a function of measuring and recognizing the current year, date, and time, and a function of measuring the lapse of time from an arbitrary time point. Any information acquired through measurement or the like by the sensor unit SU can be stored in the memory 30, and when such storing takes place, the information is stored in the memory 30 in a form associated with time information representing the year, date, and time of its acquisition. The time information is generated by the timer 40. The wireless processor 50 exchanges any information wirelessly with an external device, that is, a device different from the sensor unit SU.

Figure 4:
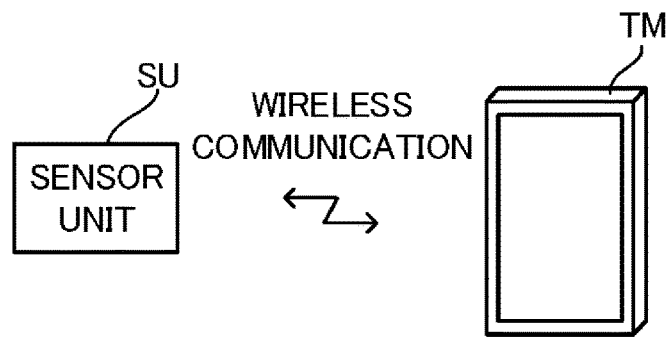
FIG. 4 is a diagram showing the sensor unit along with a terminal device.

Referring to FIG. 4, suppose here that the external device is a terminal device TM. The terminal device TM is, for example, an information terminal, mobile telephone, or personal computer. So-called smartphones belong to information terminals, mobile telephones, or personal computers. The terminal device TM too includes a wireless processor similar to the wireless processor 50, so that by use of the wireless processor 50 of the sensor unit SU and the wireless processor of the terminal device TM, bidirectional wireless communication of information is achieved between the sensor unit SU and the terminal device TM.

Figure 5:
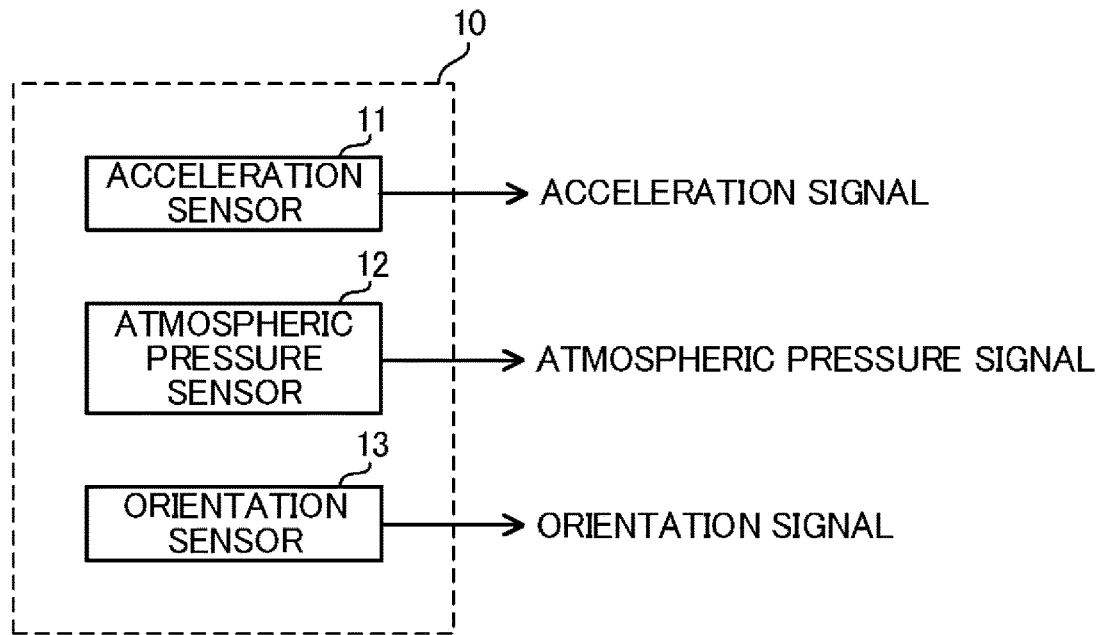
FIG. 5 is a block diagram of a sensor arrangement in the sensor unit.

FIG. 5 is a block diagram of the sensor arrangement 10. The sensor arrangement 10 includes an acceleration sensor 11, an atmospheric pressure sensor 12, and an orientation sensor 13.

Figure 6:
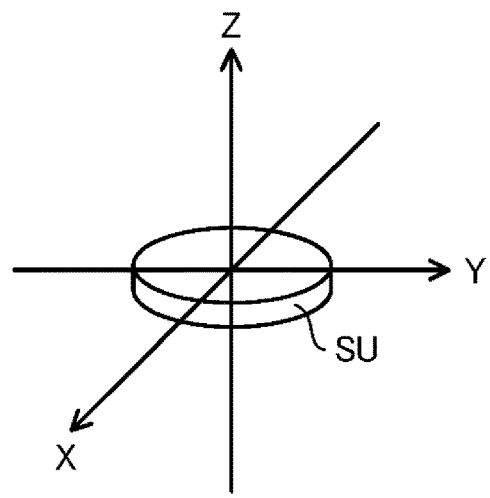
FIG. 6 is a diagram showing a relationship, to the sensor unit, of the three axes of an acceleration sensor.

The acceleration sensor 11 is a three-axis acceleration sensor; it senses, in the X-, Y-, and Z-axis directions individually, the acceleration resulting from the acceleration sensor 11 (hence the housing 3 or the sensor unit SU) being moved, and outputs acceleration signal representing the sensed acceleration along those axes respectively. The acceleration signal output from the acceleration sensor 11 is composed of an X-axis acceleration signal representing the acceleration in the X-axis direction, a Y-axis acceleration signal representing the acceleration in the Y-axis direction, and a Z-axis acceleration signal representing the acceleration in the Z-axis direction. As shown in FIG. 6, the X, Y, and Z axes are perpendicular to each other. Here, it is assumed that the axis of the cylinder as the exterior shape of the housing 3 coincides with the Z axis, and that the X, Y, and Z axes perpendicularly intersect with each other at the center of the cylinder.

The atmospheric pressure sensor 12 senses the atmospheric pressure at the site where the sensor unit SU is located, and outputs an atmospheric pressure signal representing the sensed atmospheric pressure. Since the altitude and the atmospheric pressure are in a definite relationship, the microcomputer 20 can calculate the altitude based on the atmospheric pressure signal. Here, the altitude denotes the altitude of the site where the sensor unit SU is located relative to the ground at 0 m (meters) above sea level.

The orientation sensor 13 senses the orientation in which the sensor unit SU is situated, and outputs an orientation signal representing the sensed orientation. A three-axis geomagnetic sensor that can sense geomagnetism in directions parallel to the X, Y, and Z axes individually can be used to form the orientation sensor 13. Here, the orientation in which the sensor unit SU is situated denotes the orientation of the line pointing from the center of the first base of the sensor unit SU to the center of its second base. The first base denotes, of the bases of the cylinder as the exterior shape of the housing 3, one previously defined base, and the second base denotes the other base. Based on the orientation signal from the orientation sensor 13, the microcomputer 20 generates and acquires orientation information indicating the orientation in which the sensor unit SU is situated.

Second Embodiment

A second embodiment of the present invention will be described. The second embodiment—and also a third and a fourth embodiment, which will be described later—is based on the first embodiment. Accordingly, as to such features of the second embodiment as are given no particular mention, the relevant description given for the first embodiment, unless inconsistent, applies equally to the second to fourth embodiments. As to such features of the second embodiment as contradict between the first and second embodiment, their description given for the second embodiment prevails (the same is true with the third and fourth embodiments described later). Unless inconsistent, two or more of the first to fourth embodiments can be implemented in combination.

The second embodiment deals with a method for measuring the muscular strength or the like of a subject by use of a measurement device including the sensor unit SU (the significance of muscular strength will be discussed later). A person whose muscular strength or the like is measured is called a subject, who is thus actually the user of the sensor unit SU. Whereas the method disclosed in Non-Patent Document 1 requires at least two monitoring points, the sensor unit SU permits evaluation of muscular strength or the like by use of a single acceleration sensor. It is considered that monitoring equivalent to that performed at two places (hip and knee) according to Non-Patent Document 1 can be performed with a single acceleration sensor appropriately by measuring acceleration at a part of the body that exhibits a correlation with the sum of the hip and knee moments, and as that part of the body, the chest front is most suitable or suitable. On the other hand, in an STS movement, it is important that people stand up vigorously with the power of the lower body alone. Accordingly, the most suitable or a suitable approach is to measure acceleration in a movement of standing up vigorously with the forearms crossed before the chest with an acceleration sensor attached to (for example, kept in close contact with) the subject's arm or chest.

Figure 7A:
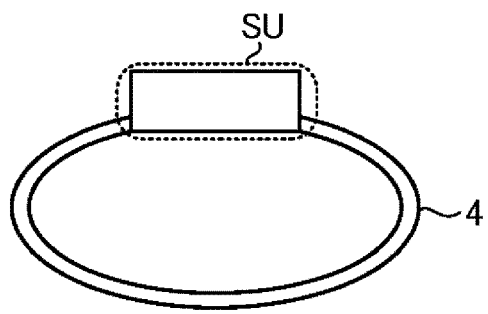
FIGS. 7A and 7B are diagram showing a structure of a measurement device according to a second embodiment of the present invention.
Figure 7B:
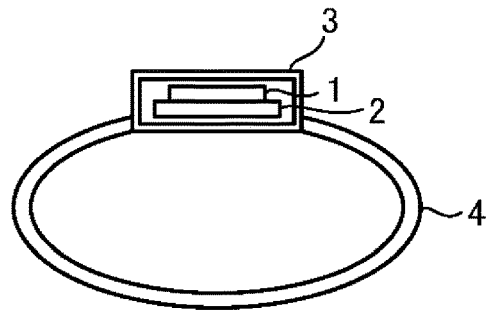

A description will now be given of the structure of a measurement device for measuring muscular strength or the like by use of such a movement. FIG. 7A is an exterior side view of the measurement device according to this embodiment. FIG. 7B is a schematic diagram showing the structure inside the housing 3 of the measurement device. The measurement device includes a sensor unit SU, which comprises a component group 1, a circuit board 2, and a housing 3, and an attachment band 4.

Figure 8:
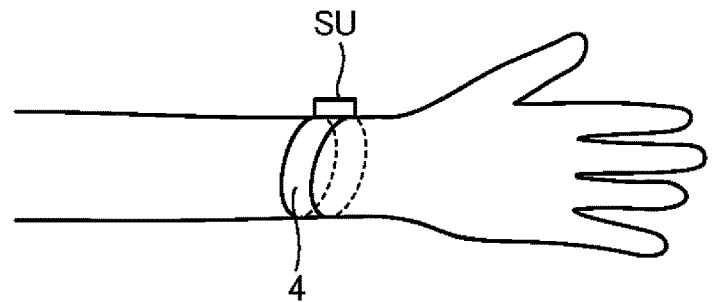
FIG. 8 is a diagram showing the measurement device in FIG. 7A attached to a subject.

The housing 3 is fitted with an attachment band 4 generally in the shape of a ring. The attachment band 4 is formed of, for example, rubber, resin, metal, or a combination of more than one of those. The attachment band 4 is provided to allow the sensor unit SU (that is, the housing 3 having the component group 1 and the circuit board 2 housed in it) to be attached and fastened to the human body as a subject. Here, for the sake of concrete description, it is assumed that, as shown in FIG. 8, the sensor unit SU is, like a wrist watch or a wrist band, wound around the subject's wrist by use of the attachment band 4. Thus, one face of the housing 3 (one of the bases of the cylindrical shape) is kept in close contact with, and is fastened to, the subject's wrist. It is however also possible, without using the attachment band 4, to keep the housing 3 in close contact with, and fasten it to, the subject's chest such that one face of the housing 3 makes direct contact with the skin of the subject's chest.

Figure 9:
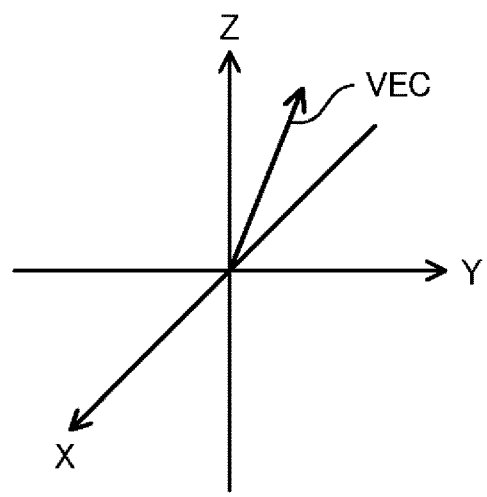
FIG. 9 is a diagram showing the three axes of an acceleration sensor in the measurement device in FIG. 7A along with a sensed acceleration vector.

While the housing 3 is kept in close contact with, and is fastened to, the subject, the acceleration sensor 11 is fixed at a predetermined position inside the housing 3; thus, the acceleration sensed by the acceleration sensor 11 includes the acceleration resulting from the movement (motion) of the subject. A vector quantity can be defined which has as its different axial components the acceleration in the X-, Y-, and Z-axis directions, respectively, as sensed by the acceleration sensor 11. Thus, it can be considered that the acceleration sensor 11 senses acceleration as a vector quantity. The acceleration as a vector quantity as sensed by the acceleration sensor 11 is called an acceleration vector. In FIG. 9, a vector VEC represents an acceleration vector formed by acceleration in the X-, Y-, and Z-axis directions. That is, the X-, Y-, and Z-axis components of the acceleration vector are respectively the acceleration in the X-axis direction, the acceleration in the Y-axis direction, and the acceleration in the Z-axis direction as sensed by the acceleration sensor 11.

Based on the acceleration sensed by the acceleration sensor 11 (hereinafter referred to also as the sensed acceleration), the microcomputer 20 can estimate and derive the subject's muscular strength or the like.

A description will now be given of a method for estimating and deriving the subject's muscular strength or the like. Based on the sensed acceleration during a predetermined evaluation period including a period in which a subject performs a predetermined evaluation movement, the sensor unit SU (hence the measurement device) can evaluate and derive the subject's muscular strength or the like.

Figure 10:
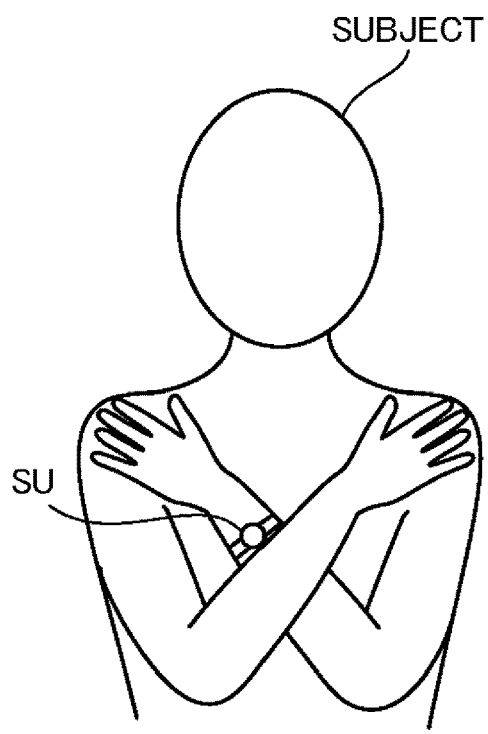
FIG. 10 is a diagram showing a subject standing upright after an evaluation movement.
Figure 11:
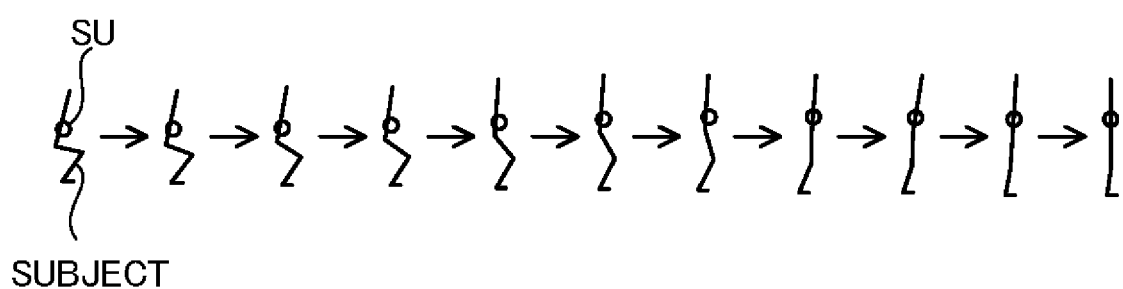
FIG. 11 is a diagram illustrating the evaluation movement.

The evaluation movement is an STS movement in which the subject stands up from a posture seated on the seating face of a chair as a predetermined face to a posture standing upright. The chair may have the seating face at any height; however, with the subject seated on the seating face of the chair, the soles of both feet of the subject should be, at the heels and toes, in contact with the floor. For example, the seating face of the chair has 20% to 30% of the subject's body height. In the evaluation movement, the subject stands up from the seating face of the chair with full force with the forearms crossed before the chest. FIG. 10 is a schematic front view of the subject who has just stood up. FIG. 11 is a simplified schematic side view of the subject during the evaluation period.

In this embodiment, one face of the housing 3 (one of the bases of the cylindrical shape) is kept in contact with, and is fastened to, the subject's wrist. Thus, with the forearms crossed before the chest, the acceleration sensor 11 is located generally in a fixed position before the subject's chest. The evaluation movement may be performed with the housing 3 located in a fixed position such that it makes direct contact with the subject's chest. That is, in the evaluation movement, with the housing 3 having the acceleration sensor 11 housed in it (or the acceleration sensor 11 itself) attached to (for example, kept in close contact with) the subject's arm or chest, the subject stands up with full force from the seating face of the chair.

In an STS movement, acceleration changes chiefly in the vertical direction, and the change of acceleration in the vertical direction includes information reflecting the subject's muscular power. However, depending on how the housing 3 is attached to the subject, the relation ship of the X-, Y-, and Z-axis directions in the acceleration sensor 11 to the vertical direction is highly likely to vary in different ways. Accordingly, in the sensor unit SU, instead of the acceleration in the X-, Y-, and Z-axis directions being evaluated individually, the magnitude of the acceleration vector is evaluated. The magnitude of an acceleration vector is called an acceleration absolute value, and a signal that has as its signal value an acceleration absolute value is called an acceleration absolute value signal. In this embodiment, unless otherwise stated, an acceleration absolute value is understood as an acceleration absolute value during an evaluation period, and an acceleration absolute value signal is understood as a signal that has as its signal value an acceleration absolute value during an evaluation period.

Figure 12:
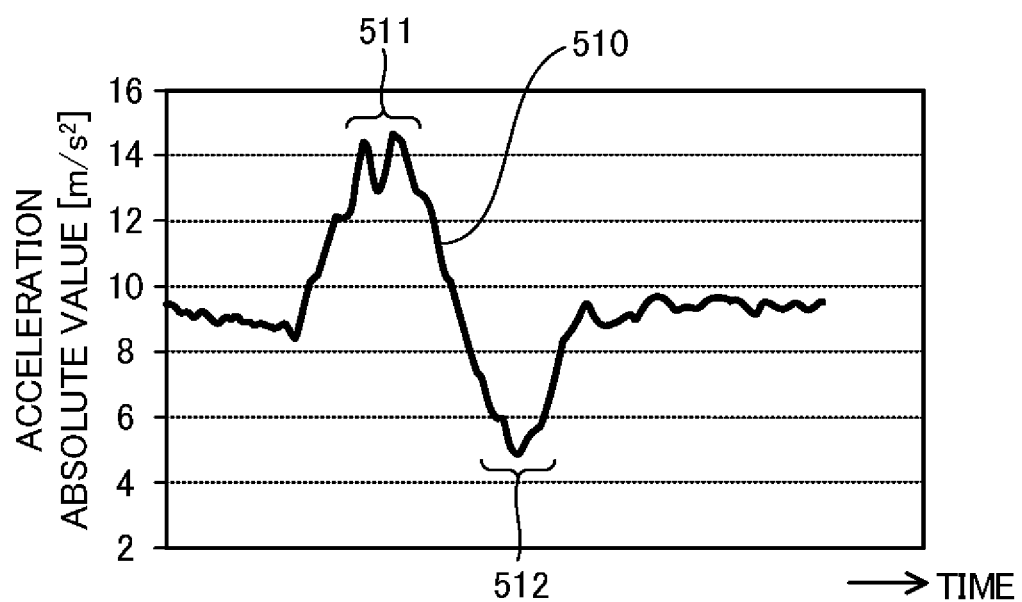
FIG. 12 is a waveform diagram of an acceleration absolute value signal based on a sensing result from the acceleration sensor.

FIG. 12 shows the waveform of an acceleration absolute value signal 510 observed when a subject performed an evaluation movement (in other words, the signal waveform of an acceleration absolute value). In the graph in FIG. 12, the horizontal axis represents time, and the vertical axis represents acceleration absolute value (the same is true with FIG. 13, which will be referred to later). The subject who gave the signal 510 was one of people without any disability, who generally exhibit, in an STS movement, large changes in the acceleration absolute value when the buttocks leave the chair and immediately before the subject halts upright. In FIG. 12, the period in which the signal 511 appears corresponds to the period in which the buttocks leave the chair and, after a while, the period in which the signal 512 appears corresponds to the period immediately before halting upright. Prior to the period in which the signal 511 appears, the period in which the acceleration absolute value remains generally at 9.8 m/s$^2$ is the period before the subject stands up from the chair (for example, the period in which the subject is seated at rest on the chair). The acceleration sensor 11 is configured as a sensor that can sense acceleration due to gravity, and thus, in the period before the subject stands up from the chair (for example, the period in which the subject is seated at rest on the chair), only gravitational acceleration is sensed by the acceleration sensor 11.

In this embodiment, the sampling frequency of the acceleration sensor 11 (that is, the reciprocal of the sensing period at which acceleration is sensed periodically) is set at 200 Hz (hertz). The sampling frequency of the acceleration sensor 11 can be set at other than 200 Hz, in which case the filtering described later can be optimized according to the sampling frequency.

Generally, the acceleration sensor 11 is sensitive to extraneous noise; even if the housing 3 is firmly fastened to the chest or arm, it responds, too sensitively, even to clothes rustling and skin movement. With this taken into consideration, in the sensor unit SU, the acceleration absolute value signal which represents the very acceleration sensed by the acceleration sensor 11 is subjected to filtering. This filtering is low-pass filtering whereby, of the acceleration absolute value signal, signal components of comparatively low frequencies are attenuated and signal components of comparatively high frequencies are passed. In this embodiment, the filtering involves low-pass filtering using a fourth-order Butterworth low-pass digital filter, and the cutoff frequency of the low-pass filtering is set at 5 Hz.

Figure 13:
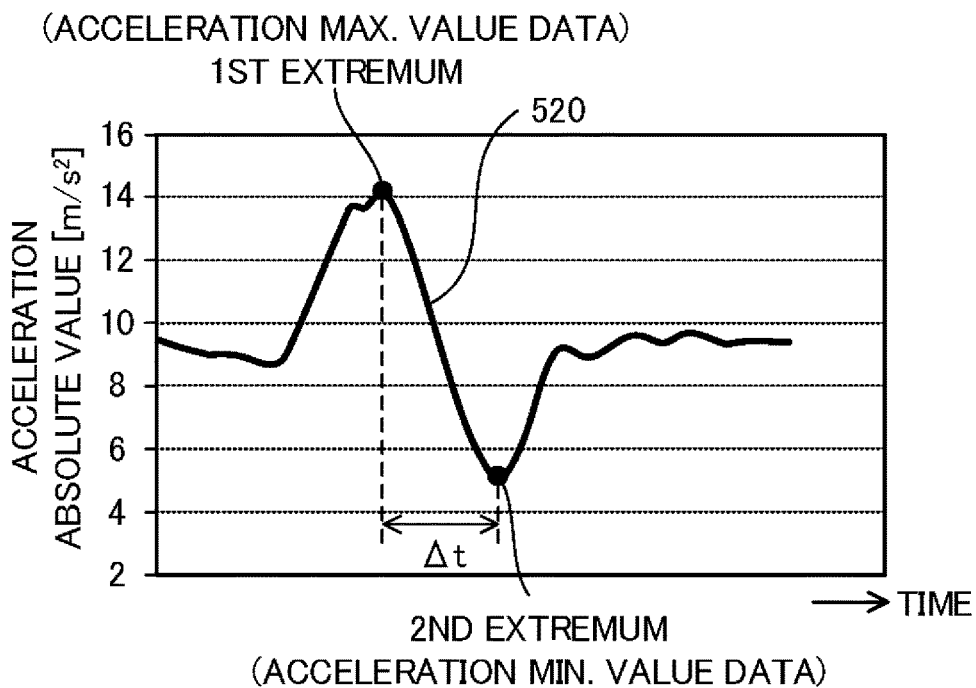
FIG. 13 is a waveform diagram of a signal obtained by applying filtering to the acceleration absolute value signal in FIG. 12.
Figure 14:
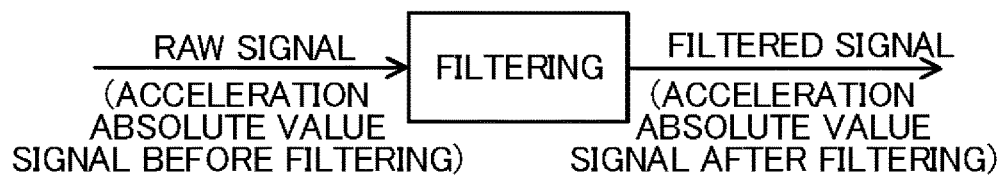
FIG. 14 is a diagram showing a relationship between a raw signal and a filtered signal.

The waveform of the signal obtained by applying filtering to the acceleration absolute value signal 510 shown in FIG. 12, which is the acceleration absolute value signal before filtering, that is, the waveform of the acceleration absolute value signal 520 after filtering, is shown in FIG. 13. In the following description, for the sake of simple and clear description, as shown in FIG. 14, an acceleration absolute value signal before filtering, like the acceleration absolute value signal 510, is called a raw signal, and an acceleration absolute value signal after filtering, like the acceleration absolute value signal 520, is called a filtered signal. The signal value of a raw signal or a filtered signal is an acceleration absolute value.

During the evaluation period, the acceleration absolute value, which is the signal value of the filtered signal, first remains generally at a constant value (9.8 m/s$^2$) and then increases to reach a first extremum around the time point that the subject's buttocks leave the chair; thereafter it decreases to reach the constant value and then further decreases to reach a second extremum around the time point immediately before the subject halts upright; thereafter it increases to reach the constant value.

The first extremum is the maximum signal value of the filtered signal during the evaluation period, and is called the acceleration maximum value data. In the example shown in FIG. 13, the acceleration maximum value data is about 14.3 m/s$^2$. The second extremum is the minimum signal value of the filtered signal during the evaluation period, and is called the acceleration minimum value data. In the example shown in FIG. 13, the acceleration minimum value data is about 5.0 m/s$^2$. For the filtered signal, the time difference between the time point that the signal value equals the first extremum and the time point that the signal value equals the second extremum is represented by Δt (the use of Δt will be discussed later).

The sensed acceleration from the acceleration sensor 11 contains a static component and an inertial component. The static component contains an acceleration component due to gravity and an acceleration component due to an extraneous force other than the subject's movement. Here, it is assumed that the sensor unit SU is used on the earth, and that the magnitude of the acceleration component due to gravity equals 9.8 m/s$^2$. Needless to say, gravitational acceleration acts in the vertical direction. The inertial component is an acceleration component due to the subject's movement, and is the necessary component in the STS movement. In an ordinary STS movement, it is considered that no extraneous force is acting and that gravitation is constant; thus, the inertial component can be considered equal to the sensed acceleration minus the acceleration component due to gravity.

The microcomputer 20 includes a filter (unillustrated) that applies filtering to the raw signal to generate the filtered signal, and derives, based on the filtered signal based on the raw signal during the evaluation period, various indices related to the subject's muscular power or the like. The filter may be, instead of being provided in the microcomputer 20, inserted between the acceleration sensor 11 and the microcomputer 20.

[Deriving Index P$_1$]

The indices derived based on the filtered signal can include index P$_1$. Index P$_1$ is given by, for example, $P_1$=(Acceleration Maximum Value Data−Gravitational Acceleration)/(Body Weight×Muscle Percentage), that is, $$P_1=(ACC_{MAX}-9.8)/(WEIGHT \times MS_{PER}). \quad (1A)$$

Here, $ACC_{MAX}$ represents the acceleration maximum value data in the unit of m/s$^2$, WEIGHT represents the subject's body weight, and $MS_{PER}$ represents the subject's muscle percentage. Since the subject's muscle percentage indicates the proportion of the subject's muscle mass in the subject's body weight, index P$_1$ can be expressed also as $P_1$=(Acceleration Maximum Value Data−Gravitational Acceleration)/Muscle Mass.

That is, formula (1A) can be rewritten as formula (1B) below:

$$P_1=(ACC_{MAX}-9.8)/MS_{AMT}. \quad (1B)$$

Here, $MS_{AMT}$ represents the subject's muscle mass (that is, the weight of the muscle contained in the subject's body).

The microcomputer 20 can derive index P$_1$ according to formula (1A) or (1B). It is assumed that, when index P$_1$ is derived according to formula (1A) or (1B), the subject's body weight WEIGHT and muscle percentage $MS_{PER}$, or the subject's muscle mass $MS_{AMT}$, has previously been fed to the microcomputer 20.

Inconveniently, it is generally not easy to know an accurate muscle percentage or muscle mass. If, however, we assume that the human body is formed of "muscle", "fat", and "bone and organs" and that the "bone and organs" are constant among subjects irrespective of differences in their physical constitution, then it is possible to derive index P$_1$ by using, instead of a muscle percentage or muscle mass, a body fat percentage or body fat mass, which is comparatively easy to measure and acquire.

Specifically, for example, the microcomputer 20 can derive index P$_1$ according to formula (2A) or (2B).

$$P_1=(ACC_{MAX}-9.8)/WEIGHT \times (1-BF_{PER}) \quad (2A)$$

$$P_1=(ACC_{MAX}-9.8)/(WEIGHT-BF_{AMT}) \quad (2B)$$

Here, $BF_{PER}$ represents the subject's body fat percentage, and $BF_{AMT}$ represents the subject's body fat mass (that is, the weight of the body fat contained in the subject's body). Thus, in formulae (2A) and (2B), for the sake of simplicity, the weight of "bone and organs" is ignored. It is assumed that, when index P$_1$ is derived according to formula (2A) or (2B), the subject's body weight WEIGHT and body fat percentage $BF_{PER}$, or the subject's body weight WEIGHT and body fat mass $BF_{AMT}$, have previously been fed to the microcomputer 20.

For another example, the microcomputer 20 can derive index P$_1$ according to formula (2C) or (2D).

$$P_1=(ACC_{MAX}-9.8)/WEIGHT \times (1-BF_{PER}-K_{A1}) \quad (2C)$$

$$P_1=(ACC_{MAX}-9.8)/(WEIGHT-BF_{AMT}-K_{A2}) \quad (2D)$$

Here, $K_{A1}$ represents a value that is previously defined as indicating the ratio of the weight of the "bone and organs" contained in the subject's body to the subject's body weight. $K_{A2}$ represents a value that is previously defined as indicating the weight of the "bone and organs" contained in the subject's body. Also here, it is assumed that, when index P$_1$ is derived according to formula (2C) or (2D), the subject's body weight WEIGHT and body fat percentage $BF_{PER}$, or the subject's body weight WEIGHT and body fat mass $BF_{AMT}$, have previously been fed to the microcomputer 20.

In formulae (1A), (1B), and (2A) to (2D), the denominator in the right-hand side represents the subject's muscle mass itself or an approximate value of the subject's muscle mass. Thus, index $P_1$ represents the acceleration maximum value per unit amount of muscle of a subject in an STS movement as an evaluation movement, and this is called the muscular strength. The muscular strength depends on the subject's muscular power, and thus can be grasped as an index related to the subject's muscular power (a muscular power index). The muscular power divides roughly into the power of those muscles which work on a continuous basis and the power of those muscles which work on an instantaneous basis (that is, explosive power), and the muscular power based on the result of acceleration sensing is considered to belong to the latter.

Index $P_1$ can be grasped as indicating the efficiency of use of muscles rather than the magnitude of the muscle mass. That is, a high index $P_1$ indicates efficient use of muscles; thus, a high index $P_1$ can be taken as pointing to an excellent muscular strength. For example, even apparently well-muscled people, if they exhibit a low index $P_1$, may not be using their muscles efficiently. In a case where index $P_1$ is derived according to, for example, formula (2A) or the like, it is more difficult for people with comparatively heavy body weights or with comparatively low body fat percentages than for other people to attain a high index $P_1$. In that case, for people with comparatively heavy body weights or with comparatively low body fat percentages to yield excellent results with respect to index $P_1$, they need to attain higher acceleration maximum values than other people (that is, they need to stand up more quickly).

Figure 15:
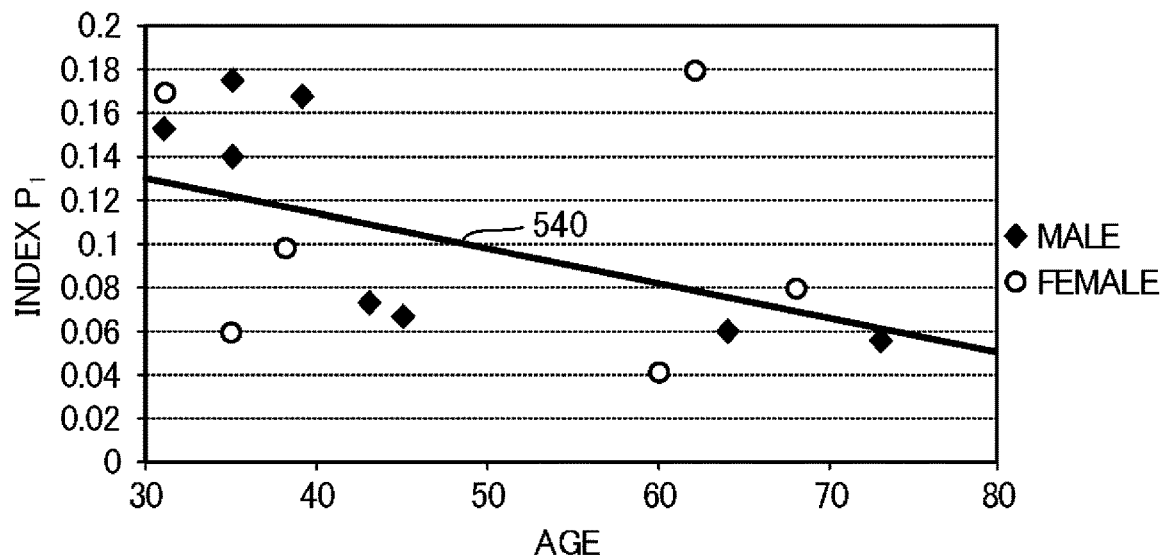
FIG. 15 is a diagram showing a distribution of indices ($P_1$) derived for a plurality of subjects, with age along the horizontal axis.

FIG. 15 shows the results of experiments conducted in connection with index $P_1$. In these experiments, a plurality of subjects performed an evaluation movement, and for each subject, index $P_1$ was derived in the manner described above. Index $P_1$ was derived according to formula (2A). In FIG. 15, the subjects' age is taken along the horizontal axis, and the derived index $P_1$ is taken along the vertical axis. Of the plurality of subjects, eight were male and six were female, and their ages spanned widely from thirties to seventies. In FIG. 15, black diamonds correspond to male subjects, and hollow circles correspond to female subjects (the same is true with FIG. 16, which will be referred to later). The experiments reveal that, at or over a predetermined age (for example, 30), as the subjects' age increases, index $P_1$ tends to decrease. This tendency is considered to reflect the actual tendency of the muscular power declining with increasing age. Also from this fact, it is seen that index $P_1$ is an adequate indicator of the condition of the muscular power of subjects.

In FIG. 15, a straight line 540 represents the average values of index $P_1$ at different ages in the experiments, and is expressed by the formula y=ax+b. In this formula, y represents the value of index $P_1$, x represents the subject's age, and a and b are the coefficients that define the straight line 540. Finding the straight line 540 through the experiments described above with a larger number of subjects can bring the values of the coefficients a and b closer to those which reflect actualities. Although, here, y is taken as a linear function of x, it is also possible to take y as a high-degree function (quadratic or higher-degree function) of x.

[Deriving Index $P_2$]

The indices derived based on the filtered signal can include index $P_2$. Index $P_2$ is given by, for example, $P_2$=(Acceleration Maximum Value Data−Gravitational Acceleration)/(Body Weight×Body Fat Percentage), that is, $$P_2=(ACC_{MAX}-9.8)/(WEIGHT \times BF_{PER}). \quad (3A)$$

Here, $ACC_{MAX}$ represents the acceleration maximum value data in the unit of m/s$^2$, and the subject's body fat percentage $BF_{PER}$ is the proportion of the subject's body fat mass in the subject's body weight WEIGHT. Thus, index $P_2$ can be expressed also as $P_2$=(Acceleration Maximum Value Data−Gravitational Acceleration)/Body Fat Mass.

That is, formula (3A) can be rewritten as formula (3B) below:

$$P_2=(ACC_{MAX}-9.8)/BF_{AMT}. \quad (3B)$$

The microcomputer 20 can derive index $P_2$ according to formula (3A) or (3B). It is assumed that, when index $P_2$ is derived according to formula (3A) or (3B), the subject's body weight WEIGHT and body fat percentage $BF_{PER}$, or the subject's body fat mass $BF_{AMT}$, has previously been fed in the microcomputer 20.

Index $P_2$ represents the acceleration maximum value per unit amount of body fat of a subject in an STS movement as an evaluation movement. Generally, it is easier for thin, well-muscled people than other people to attain a high index $P_2$. Thus, index $P_2$ can be used as an indicator of tendency toward obesity.

Figure 16:
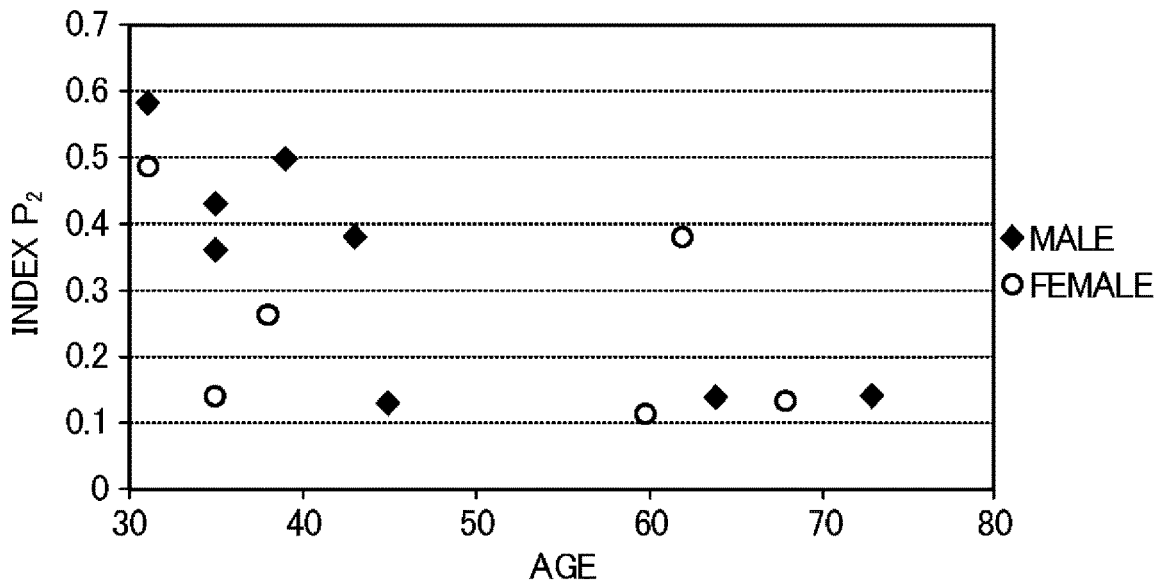
FIG. 16 is a diagram showing a distribution of indices ($P_2$) derived for a plurality of subjects, with age along the horizontal axis.

FIG. 16 shows the indices $P_2$ derived for the plurality of subjects based on the acceleration maximum value data obtained through the above-described experiments corresponding to FIG. 15. In FIG. 16, the subjects' age is taken along the horizontal axis, and the derived index $P_2$ is taken along the vertical axis. Handling similar to that applied to index $P_1$ can be applied to index $P_2$; it is thereby possible to derive, from the indices $P_2$ found for the plurality of subjects, a relational equation between their age and index $P_2$.

[Deriving Index $P_3$]

The indices derived based on the filtered signal can include index $P_3$. Index $P_3$ is derived based on the waveform of the filtered signal during the evaluation period. For example, index $P_3$ is calculated according to formula (4A), (4B), or (4C) below.

$$P_3 = k_{B1}(ACC_{MAX}-9.8)-k_{B2} \cdot \Delta t \quad (4A)$$

$$P_3 = k_{B1}(ACC_{MAX}-9.8)/\Delta t \quad (4B)$$

$$P_3 = k_{B1}/\Delta t \quad (4C)$$

The symbols $k_{B1}$ and $k_{B2}$ represent previously defined positive coefficients. What $\Delta t$ represents is as mentioned above with reference to FIG. 13. It is considered that, the higher the subjects' muscular power (explosive power) is, and thus the quicker they stand up, the greater the acceleration maximum value data $ACC_{MAX}$, and the shorter the time $\Delta t$. Accordingly, like index $P_1$, index $P_3$ too depends on the subject's muscular power, and thus can be grasped as an index related to the subject's muscular power (a muscular power index).

[Collecting Experiment Data]

By use of the sensor unit SU, experiment data collection can be performed in a manner as described below. Experiment data collection is performed, for example, at the stage of design or manufacture of the sensor unit SU before it is, as a product, used by consumers (general consumers and care-taking and medical professionals). Experiment data collection involves repeating unit experiments. In a unit experiment, one subject of a given age performs an evaluation movement, and for this subject, indices $P_1$, $P_2$, and $P_3$ are derived in the manner described above. Similar unit experiments are conducted with a large number of subjects of varying ages.

A first to an nth age group are defined such that they are mutually exclusive. Here, it is assumed that n is an integer of 2 or more, and that, for any integer i, the ages belonging to the (i+1)th age group are higher than those belonging to the ith age group.

As to a plurality of indices $P_1$ derived for a plurality of subjects belonging to the ith age group, the average value and the positive square root of the dispersion are represented by $AVE_{P1}[i]$ and $\sigma_{P1}[i]$ respectively.

As to a plurality of indices $P_2$ derived for a plurality of subjects belonging to the ith age group, the average value and the positive square root of the dispersion are represented by $AVE_{P2}[i]$ and $\sigma_{P2}[i]$ respectively.

As to a plurality of indices $P_3$ derived for a plurality of subjects belonging to the ith age group, the average value and the positive square root of the dispersion are represented by $AVE_{P3}[i]$ and $\sigma_{P3}[i]$ respectively.

In experiment data collection, from the results of unit experiments with a large number of subjects, a set of classification data (classification data set) is derived which comprises $AVE_{P1}[1]$ to $AVE_{P1}[n]$, $\sigma_{P1}[1]$ to $\sigma_{P1}[n]$, $AVE_{P2}[1]$ to $AVE_{P2}[n]$, $\sigma_{P2}[1]$ to $\sigma_{P2}[n]$, $AVE_{P3}[1]$ to $AVE_{P3}[n]$, and $\sigma_{P3}[1]$ to $\sigma_{P3}[n]$. The calculations for deriving the classification data set may be performed in a calculation device (unillustrated) separate from the sensor unit SU.

The classification data set can be derived separately for males and females. In the following description, however, for the sake of simple description, unless otherwise stated, it is supposed that all subjects are male and the classification data set is one for males.

[Example of Use of the Measurement Device]

Figure 17:
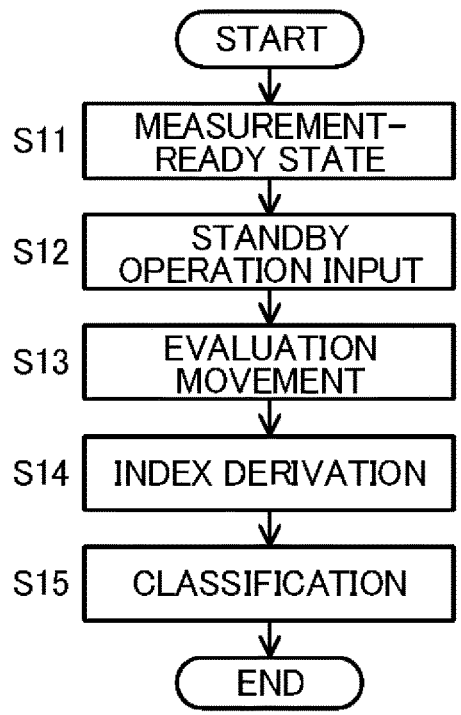
FIG. 17 is a diagram showing a specific flow of an example of use of the measurement device.

With reference to FIG. 17, a description will now be given of a specific flow of an example of how the sensor unit SU is used, including how the classification data set is used. The operations at steps S11 through S15 in FIG. 17 are performed after a classification data set is acquired.

First, at step S11, a subject and the sensor unit SU are brought into a measurement-ready state. In the measurement-ready state, the subject is seated on a predetermined chair, and one face of the housing 3 of the sensor unit SU is brought into contact with, and is fastened to, the subject's wrist (or chest).

Next, at step S12, the subject or another person inputs a standby operation to the sensor unit SU. The sensor unit SU can recognize whether or not a standby operation has been input. The standby operation is, for example, an operation of pressing an unillustrated operation button provided on the housing 3. In this case, the sensor unit SU has only to monitor whether the operation button is depressed. The operation button may be one on a touch panel. For another example, the standby operation may be inputting a predetermined operation to the terminal device TM (see FIG. 4) which is wirelessly connected to the sensor unit SU. In this case, on receiving the input of the predetermined operation, the terminal device TM conveys the event to the sensor unit SU, and thereby the input of the standby operation is recognized.

After or before the input of the standby operation, the subject assumes a posture with the forearms crossed before the chest. Promptly after the input of the standby operation, at step S13, the subject performs the evaluation movement described above. The microcomputer 20 can take the time point of the input of the standby operation as the time point of the start of the evaluation period. The evaluation period can have a predetermined length of time (for example, 10 seconds). In this case, the microcomputer 20 takes the time point that a predetermined time has elapsed from the time point of the input of the standby operation as the time point of the end of the evaluation period. Or the evaluation period may be ended at the time point at which the acceleration minimum value data is observed in the filtered signal.

After the expiry of the evaluation period, at step S14, based on the sensing result from the acceleration sensor 11 during the evaluation period, the microcomputer 20 derives all or part of indices $P_1$ to $P_3$ described above. Then, at step S15, the microcomputer 20 performs classification based on the indices derived at step S14 and the classification data set. The following description of classification assumes that the classification data set is previously stored in a non-volatile memory (unillustrated) incorporated in the microcomputer 20 or the memory 30.

Consider, for example, a case where a subject's age belongs to the ith age group (where i is an integer of 1 or more but n or less). Information that the subject's age belongs to the ith age group has previously been fed to the sensor unit SU.

Figure 18:
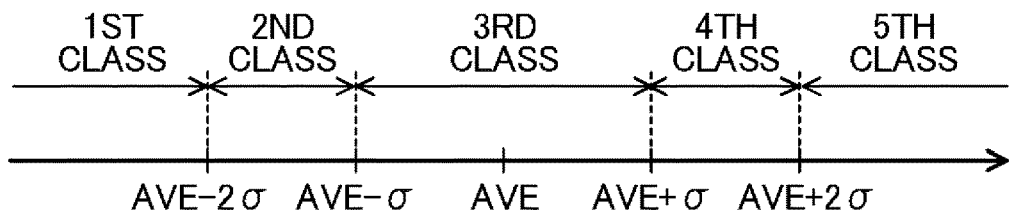
FIG. 18 is a diagram illustrating classification.

In this case, for example as shown in FIG. 18, in classification as to index $P_1$ derived at step S14, with respect to a given index $P_1$, if it fulfills $$P_1 < AVE_{P1}[i] - 2 \cdot \sigma_{P1}[i],$$

it is sorted into a first class; if it fulfills $$AVE_{P1}[i] - 2 \cdot \sigma_{P1}[i] \leq P_1 \leq AVE_{P1}[i] - \sigma_{P1}[i],$$

it is sorted into a second class; if it fulfills $$AVE_{P1}[i] - \sigma_{P1}[i] < P_1 < AVE_{P1}[i] + \sigma_{P1}[i],$$

it is sorted into a third class; if it fulfills $$AVE_{P1}[i] + \sigma_{P1}[i] \leq P_1 \leq AVE_{P1}[i] + 2 \cdot \sigma_{P1}[i],$$

it is sorted into a fourth class; and if it fulfills $$AVE_{P1}[i] + 2 \cdot \sigma_{P1}[i] < P_1,$$

it is sorted into a fifth class.

The value $(AVE_{P1}[i] - 2 \cdot \sigma_{P1}[i])$, the value $(AVE_{P1}[i] - \sigma_{P1}[i])$, the value $(AVE_{P1}[i] + \sigma_{P1}[i])$, and the value $(AVE_{P1}[i] + 2 \cdot \sigma_{P1}[i])$ for each age group serve as predetermined reference values in classification as to index $P_1$.

Likewise, for example, in classification as to index $P_2$ derived at step S14, with respect to a given index $P_2$, if it fulfills $$P_2 < AVE_{P2}[i] - 2 \cdot \sigma_{P2}[i],$$

it is sorted into a first class; if it fulfills $$AVE_{P2}[i] - 2 \cdot \sigma_{P2}[i] \leq P_2 \leq AVE_{P2}[i] - \sigma_{P2}[i],$$

it is sorted into a second class; if it fulfills $$AVE_{P2}[i] - \sigma_{P2}[i] < P_2 < AVE_{P2}[i] + \sigma_{P2}[i],$$

it is sorted into a third class; if it fulfills $$AVE_{P2}[i] + \sigma_{P2}[i] \leq P_2 \leq AVE_{P2}[i] + 2 \cdot \sigma_{P2}[i],$$

it is sorted into a fourth class; and if it fulfills $$AVE_{P2}[i] + 2 \cdot \sigma_{P2}[i] < P_2,$$

it is sorted into a fifth class.

The value $(AVE_{P2}[i] - 2 \cdot \sigma_{P2}[i])$, the value $(AVE_{P2}[i] - \sigma_{P2}[i])$, the value $(AVE_{P2}[i] + \sigma_{P2}[i])$, and the value $(AVE_{P2}[i] +$ $2 \cdot \sigma_{P2}[i]$) for each age group serve as predetermined reference values in classification as to index $P_2$.

Likewise, for example, in classification as to index $P_3$ derived at step S14, with respect to a given index $P_3$, if it fulfills $$P_3 < AVE_{P3}[i] - 2 \cdot \sigma_{P3}[i],$$

it is sorted into a first class; if it fulfills $$AVE_{P3}[i] - 2 \cdot \sigma_{P3}[i] \leq P_3 \leq AVE_{P3}[i] - \sigma_{P3}[i],$$

it is sorted into a second class; if it fulfills $$AVE_{P3}[i] - \sigma_{P3}[i] < P_3 < AVE_{P3}[i] + \sigma_{P3}[i],$$

it is sorted into a third class; if it fulfills $$AVE_{P3}[i] + \sigma_{P3}[i] \leq P_3 \leq AVE_{P3}[i] + 2 \cdot \sigma_{P3}[i],$$

it is sorted into a fourth class; and if it fulfills $$AVE_{P3}[i] + 2 \cdot \sigma_{P3}[i] < P_3,$$

it is sorted into a fifth class.

The value ($AVE_{P3}[i] - 2 \cdot \sigma_{P3}[i]$), the value ($AVE_{P3}[i] - \sigma_{P3}[i]$), the value ($AVE_{P3}[i] + \sigma_{P3}[i]$) and the value ($AVE_{P3}[i] + 2 \cdot \sigma_{P3}[i]$) for each age group serve as predetermined reference values in classification as to index $P_3$.

Any information recognizable by the sensor unit SU, including what is derived at step S14 and what results from the classification at step S15, may be transmitted wirelessly from the sensor unit SU to the terminal device TM, or may be displayed on a display screen comprising a liquid crystal display panel or the like. Here, the display screen may be one that can be provided on the housing 3 of the sensor unit SU, or may be one provided on the terminal device TM. What is displayed on the display screen is controlled by a display controller (unillustrated) provided in the sensor unit SU or in the terminal device TM.

For example, when an index $P_1$ is sorted into the third class, an indication of average muscular strength is displayed on the display screen. When an index $P_1$ is sorted into the fourth class, an indication of better-than-average muscular strength is displayed on the display screen. When an index $P_1$ is sorted into the fifth class, an indication of muscular strength still better than the fourth class is displayed on the display screen. When an index $P_1$ is sorted into the second class, an indication of poorer-than-average muscular strength is displayed on the display screen. When an index $P_1$ is sorted into the first class, an indication of muscular strength still poorer than the second class is displayed on the display screen. When an index $P_1$ is sorted into the first or second class, a message recommending an appropriate exercise therapy or the like may be displayed on the display screen. Also for index $P_2$ or $P_3$, what is displayed on the display screen is controlled likewise. Although, in the method described above, classification is performed among five classes, the number of classes for classification may be other than five.

Although, in the example of operation described above, it is assumed that the filtering, the derivation of indices at step S14, and the classification at step S15 are all performed in the sensor unit SU, all or part of them may be performed in the terminal device TM. In that case, part or all of the microcomputer 20 is considered to be present in the terminal device TM. In a case where classification is performed on the terminal device TM, the classification data set has previously been fed to the terminal device TM.

In this embodiment, muscular strength or the like can be measured with a simple configuration involving the use of sensing data from an acceleration sensor. The simple configuration contributes to making devices compact and inexpensive. From subjects' (users') perspective, muscular strength or the like can be measured easily by a habitual movement such as standing up from a chair, and thus their muscular power can be visualized easily on a routine basis. It is thus possible to detect a lack of physical exercise, to improve QOL (quality of life), to advise subjects on an adequate amount of exercise and the like to be aimed at so as not to be confined to bed, and hence to improve healthy life expectancy and, consequently, to reduce medical costs.

An acceleration sensor that does not sense gravitational acceleration may be used as the acceleration sensor 11, in which case, in the relevant formulae noted above, ($ACC_{MAX} - 9.8$) is to be replaced with $ACC_{MAX}$. In that case, both the first and second extrema are maxima; even then, in a similar manner as described above, the first extremum is dealt with as the acceleration maximum value data.

When the evaluation movement is performed, the acceleration sensor 11 is placed at a predetermined position where it can sense the acceleration resulting from the subject's movement, and, in the above description, the predetermined position is assumed to be before the subject's chest. This, however, is not meant to limit the predetermined position to before the subject's chest; the predetermined position may instead be before the pit of the stomach, or before the throat, of the subject.

Third Embodiment

A third embodiment of the present invention will be described.

The microcomputer 20 includes an activity amount deriver which measures and derives the amount of activity. The amount of activity denotes the amount of activity of the human body as a user (in other words, subject). To more accurately acquire acceleration occurring in every kind of physical activity of a user, it is preferable that the sensor unit SU be in as close contact as possible with the user's body.

The amount of activity is an index that indicates the amount of physical activity of a user as calculated and acquired by the sensor unit SU, and can be, for example, the amount of physical exertion (in the unit of exercise (EX)) defined as the intensity of physical exertion multiplied by the duration of physical exertion. The intensity of physical exertion is a quantity that indicates the intensity of a person's physical exertion in terms of multiples of that at rest, and is given in the unit of METs (metabolic equivalents). As the amount of activity, any other quantity commensurate with the amount of physical exertion may be calculated; for example, the amount of energy expended in an activity (in the unit of kcal) may be calculated. The amount of energy expended in an activity is calculated by multiplying the amount of physical exertion by a user's body weight (in the unit of kg) and then further multiplying the result by 1.05.

The user's biometric information is fed to the terminal device TM via a user interface (unillustrated) provided in the terminal device TM to be held in the terminal device TM, and is also transmitted to the sensor unit SU by wireless communication to be stored in the memory 30. The user's biometric information may instead be previously fed to the sensor unit SU via a user interface (unillustrated) provided in the sensor unit SU to be stored in the memory 30. The user's biometric information can include the user's sex, age, body weight, body height, body fat percentage, body fat mass, muscle percentage, muscle mass, and the like, and by using the user's biometric information, the microcomputer 20 can derive, as to the user, the amount of activity as well as indices $P_1$, $P_2$, and $P_3$.

There have been proposed various methods for deriving the amount of activity based on an acceleration signal. The microcomputer 20 can use any well-known method for deriving the amount of activity (examples including those disclosed in Japanese Patent Applications published as Nos. 2014-226161 and 2015-8806). One simple example will now be described.

Figure 19:
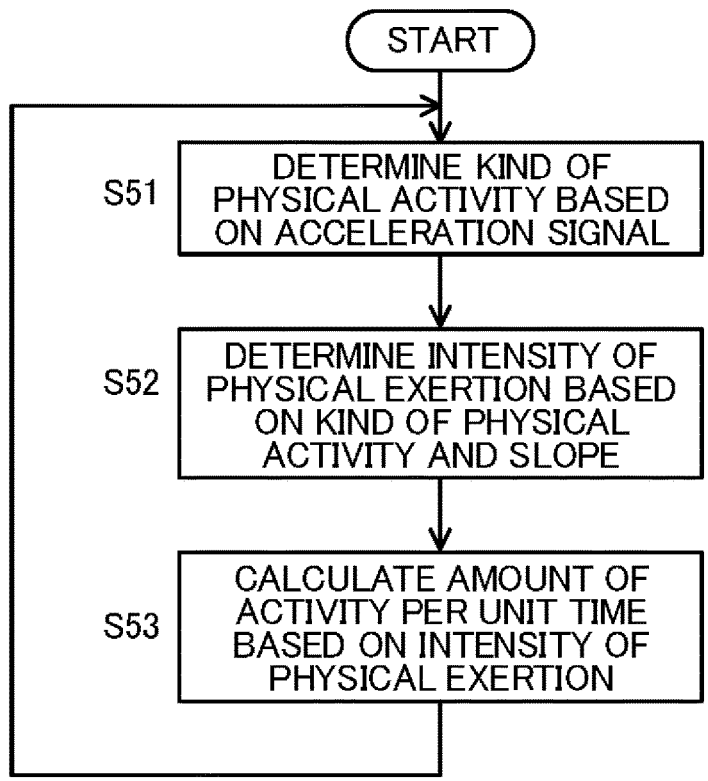
FIG. 19 is a flow chart of activity amount derivation in a third embodiment of the present invention.

FIG. 19 is a flow chart of activity amount derivation performed by the microcomputer 20. In activity amount derivation, first, at step S51, the kind of physical activity is determined based on the acceleration signal. For example, the acceleration signal changes according to whether the user wearing the sensor unit SU is at rest, is walking, or is running (for example, the acceleration vector changes its magnitude with different amplitudes and different periods). Threshold value data for distinguishes different conditions is stored in the memory 30, and based on the acceleration signal (for example, the amplitude and period with which the acceleration vector changes its magnitude) and the threshold value data, the microcomputer 20 determines whether the user's physical activity is of a first, a second, or a third kind. The first kind indicates that the user is at rest. The second kind indicates that the user is walking. The third kind indicates that the user is running.

On completion of the determination of the kind of the user's physical activity, at step S52, based on the determined kind of physical activity and a slope, the microcomputer 20 determines the intensity of physical exertion. The slope denotes the slope of the ground surface, stairway, or the like as observed when the user is walking or running on it.

For example, every time the user walks or runs 10 steps, the microcomputer 20 performs altitude sensing to sense the altitude based on the atmospheric pressure signal, and, based on the sensed altitude resulting from the previous altitude sensing and the sensed altitude resulting from the just-performed altitude sensing, calculates the slope in a cyclically updating manner. The microcomputer 20 has, though not mentioned thus far, a pedometer function for counting the number of steps taken by the user by a well-known method based on the acceleration signal. At step S52, the intensity of physical exertion is determined based on the most recent slope. The memory 30 stores a table for converting the type of physical activity and the slope to the intensity of physical exertion, and based on this table, the intensity of physical exertion is determined.

The user's step length, which is required in the calculation of the slope, has previously been fed to the sensor unit SU. Based on the number of steps counted by the pedometer function, the step length, and the altitude sensed by altitude sensing, the slope can be determined. As the step length, one to be referred to when the user is judged to be walking and one to be referred to when the user is judged to be running can be defined separately. The step length may instead be estimated from the user's body height that has previously been fed to the sensor unit SU.

Subsequent to step S52, at step S53, the microcomputer 20 calculates the amount of activity per unit time based on the intensity of physical exertion determined at step S52. For example, the amount of physical exertion (in the unit of exercise (EX)) can be calculated simply by multiplying the intensity of physical exertion by the unit time. For another example, the amount of energy expended in an activity (in the unit of kcal) can be calculated by multiplying the intensity of physical exertion by the unit time, then by the user's body weight (in the unit of kg), and further by 1.05.

By performing the unit procedure comprising steps S51 through S53 every unit time, the microcomputer 20 calculates the amount of activity cyclically for one unit time to the next.

By cumulatively adding up the amount of activity calculated every unit time, the microcomputer 20 can calculate the amount of activity during a given period which has a length corresponding to a plurality of unit times. The amount of activity in the given period can be stored in the memory 30, and chronological data of the amount of activity can be stored in the memory 30. The chronological data of the amount of activity comprises a set of amounts of activity calculated cyclically every unit time.

The memory 30 suitably comprises a volatile memory and a non-volatile memory. The volatile memory can temporarily store various kinds of data for processing by the microcomputer 20 and the like, and the non-volatile memory can store data to be held on a long-term basis. For example, the non-volatile memory stores information on past physical activities (including amounts of activity) for different dates and times, the values of indices $P_1$ to and $P_3$ derived in the past, biometric information as mentioned above, various programs, and the like.

Although the above description deals with an example where the amount of activity is derived by use of not only the results of acceleration sensing but also the results of atmospheric pressure sensing, the amount of activity may instead be derived by use of the results of acceleration sensing only. In that case, the atmospheric pressure sensor 12 may be omitted from the sensor unit SU, and the intensity of physical exertion is determined based only on the determined kind of physical activity.

An angular velocity sensor (unillustrated) that can sense individually the angular velocities of the rotation of the sensor unit SU about the X, Y, and Z axes as rotation axes may be provided in the sensor arrangement 10. In that case, the microcomputer 20 may derive the amount of activity by use of, in addition to the results of acceleration sensing, or in addition to the results of acceleration sensing and atmospheric pressure sensing, the results of angular velocity sensing. Using angular velocities makes possible accurate recognition of physical actions such as twisting of the upper body, and thus makes it possible to measure and derive the amount of activity more accurately.

[Activity Efficiency Index]

By use of the amount of activity derived in the manner described above and an index (index $P_1$ or $P_3$; hereinafter referred to as the muscular power index) related to muscular power derived by the method according to the second embodiment, the microcomputer 20 can derive an activity efficiency index, which is an index different from either the amount of activity or the muscular power index. The activity efficiency index indicates the effect of the amount of activity on the muscular power index, and can be considered to indicate the quality of a physical activity.

Figure 20:
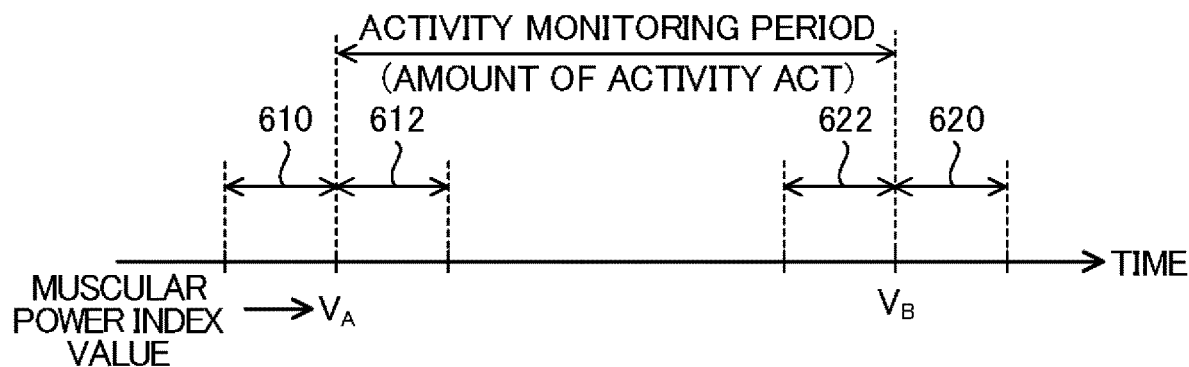
FIG. 20 is a diagram illustrating a method for deriving an activity efficiency index in the third embodiment of the present invention.
Figure 21A:
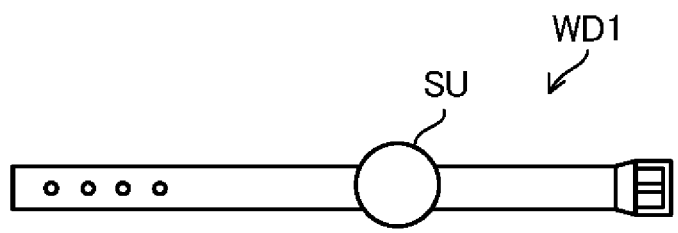
FIGS. 21A to 21D are exterior views of wearable devices according to a fourth embodiment of the present invention.
Figure 21B:
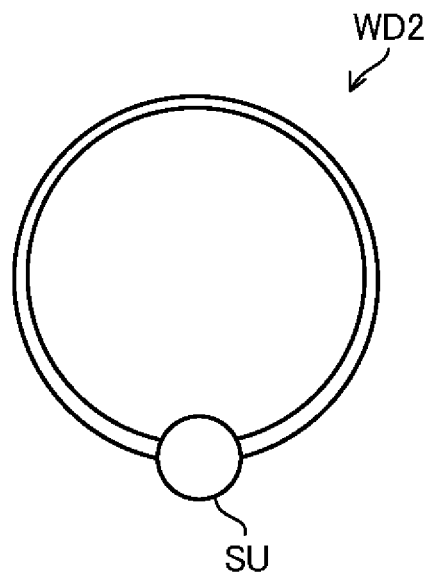
Figure 21C:
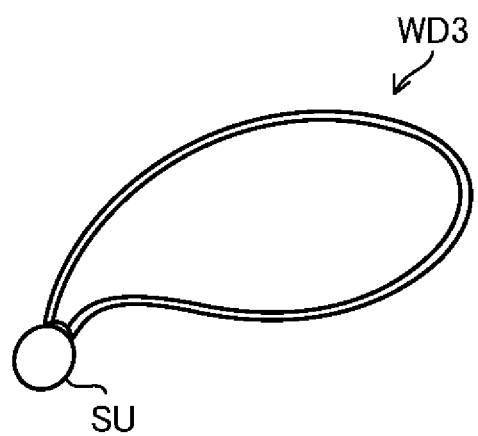
Figure 21D:
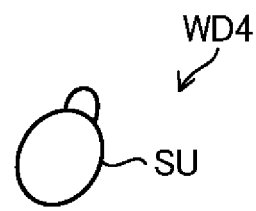

Referring to FIG. 20, a description will be given of a method for deriving the activity efficiency index. The amount of activity, as calculated by the microcomputer 20, that indicates the amount of activity during a predetermined activity monitoring period is represented by ACT. The amount of activity ACT is derived based on the sensing results from sensors during the activity monitoring period. The sensing results include at least sensing results from the acceleration sensor 11, and can also include sensing results from the atmospheric pressure sensor 12 and/or the angular velocity sensors (unillustrated).

Let $V_A$ represent the value of the muscular power index measured and derived by the method described in connection with the second embodiment in a first period relative to the start time point of the activity monitoring period. Let $V_B$ represent the value of the muscular power index measured and derived by the method described in connection with the second embodiment in a second period relative to the end time point of the activity monitoring period. As mentioned above, measuring the muscular power index requires a finite length of time to perform an evaluation movement (that is, the length of time corresponding to the evaluation period). Thus, the first and second periods just mentioned can each be understood as a period with a predetermined time width. The first period can be considered to be an evaluation period for the measurement and derivation of the muscular power index value $V_A$, and the second period can be considered to be an evaluation period for the measurement and derivation of the muscular power index value $V_B$. The microcomputer 20 derives the muscular power index value $V_A$ based on the acceleration signal (acceleration absolute value signal) during the evaluation period occurring as the first period, and derives the muscular power index value $V_B$ based on the acceleration signal (acceleration absolute value signal) during the evaluation period occurring as the second period.

The first period is determined relative to the start time point of the activity monitoring period, and usually is a period prior to the activity monitoring period.

For example, if a muscular power index value is available that was measured and derived during a period (hereinafter referred to as the period 610; see FIG. 20) from a predetermined length of time (for example, 24 hours) before the start time point of the activity monitoring period to the start time point of the activity monitoring period, that muscular power index value is dealt with as the muscular power index value $V_A$, and the evaluation period for the measurement and derivation of the muscular power index value $V_A$ is taken as the first period. If a plurality of muscular power index values are available that were measured and derived during the period 610, of those muscular power index values, the one that was measured and derived last in chronological order is dealt with as the muscular power index value $V_A$.

If no muscular power index value is available that was measured and derived during the period 610, but a muscular power index value is available that was measured and derived during a period (hereinafter referred to as the period 612; see FIG. 20) from the start time point of the activity monitoring period to a predetermined length of time (for example, 24 hours) after the start time point of the activity monitoring period, that muscular power index value is dealt with as the muscular power index value $V_A$, and the evaluation period for the measurement and derivation of the muscular power index value $V_A$ is taken as the first period. If no muscular power index value is available that was measured and derived during the period 610, and a plurality of muscular power index values are available that were measured and derived during the period 612, of those muscular power index values, the one that was measured and derived first in chronological order is dealt with as the muscular power index value $V_A$.

As an alternative method partly overlapping with the one described above, a muscular power index value that was measured and derived in a period chronologically closest to the start time point of the activity monitoring period may be dealt with as the muscular power index value $V_A$.

The second period is determined relative to the end time point of the activity monitoring period, and usually is a period posterior to the activity monitoring period. Naturally, the second period occurs later than the first period.

For example, if a muscular power index value is available that was measured and derived during a period (hereinafter referred to as the period 620) from the end time point of the activity monitoring period to a predetermined length of time (for example, 24 hours) after the end time point of the activity monitoring period, that muscular power index value is dealt with as the muscular power index value $V_B$, and the evaluation period for the measurement and derivation of the muscular power index value $V_B$ is taken as the second period. If a plurality of muscular power index values are available that were measured and derived during the period 620, of those muscular power index values, the one that was measured and derived first in chronological order is dealt with as the muscular power index value $V_B$.

If no muscular power index value is available that was measured and derived during the period 620, but a muscular power index value is available that was measured and derived during a period (hereinafter referred to as the period 622; see FIG. 20) from a predetermined length of time (for example, 24 hours) before the end time point of the activity monitoring period to the end time point of the activity monitoring period, that muscular power index value is dealt with as the muscular power index value $V_B$, and the evaluation period for the measurement and derivation of the muscular power index value $V_B$ is taken as the second period. If a plurality of muscular power index values are available that were measured and derived during the period 622, of those muscular power index values, the one that was measured and derived last in chronological order is dealt with as the muscular power index value $V_B$.

As an alternative method partly overlapping with the one described above, a muscular power index value that was measured and derived in a period chronologically closest to the end time point of the activity monitoring period may be dealt with as the muscular power index value $V_B$.

When the value of the activity efficiency index for the activity monitoring period is represented by QL, then based on the muscular power index values $V_A$ and $V_B$ and the amount of activity ACT during the activity monitoring period, QL is given by formula (5) below.

$$QL=(V_B-V_A)/ACT \qquad (5)$$

As will be understood from formula (5), the activity efficiency index represents the amount of variation of the muscular power index value per unit amount of activity during the activity monitoring period. For example, consider a case where a predetermined physical activity (such as walking) is performed during an activity monitoring period with the aim of increasing the muscular power index value. Then, if the activity efficiency index QL is comparatively high, the efficiency of the relevant physical activity in achieving its aim can be grasped as comparatively high, and if the activity efficiency index QL is comparatively low, the efficiency of the relevant physical activity in achieving its aim can be grasped as comparatively low. Specifically, when a physical activity that achieves $V_B-V_A=1$ with ACT=10 is compared with a physical activity that achieves $V_B-V_A=1$ with ACT=20, the former can be grasped as twice as efficient as the latter.

For the activity efficiency index to accurately represent "the amount of variation of the muscular power index value per unit amount of activity during an activity monitoring period", it is preferable that the length of any of the periods 610, 612, 620, and 622 (see FIG. 20) be sufficiently short as compared with that of the activity monitoring period, and is set to be equal to or shorter than the length of the activity monitoring period multiplied by a predetermined factor (if no muscular power index value $V_A$ or $V_B$ fulfilling it is available, the derivation of the activity efficiency index may be abandoned as impossible). Here, the predetermined factor has a positive value less than one, and is, for example, one part of several tens of parts to one part of several hundred parts.

The user may be allowed to freely set the start and end time points of the activity monitoring period through operation via a user interface. Here, the user interface may be one provided in the terminal device TM, or one provided in the sensor unit SU.

Any information recognized by the sensor unit SU, including the information derived by the microcomputer 20 or stored in the memory 30 (including, for example, indices $P_1$ to $P_3$, the amount of activity, chronological data of the amount of activity, the activity efficiency index, and orientation information; hereinafter referred to as unit-acquired information) can be transferred via the wireless processor 50 to the terminal device TM, and the terminal device TM can display unit-acquired information on a display screen provided on the terminal device TM. The sensor unit SU may be provided with a display screen, in which case unit-acquired information may be displayed on the display screen of the sensor unit SU.

Fourth Embodiment

A fourth embodiment of the present invention will be described. The fourth embodiment deals with applied and modified techniques that involve the use of the sensor unit SU. The techniques described in connection with the fourth embodiment can be implemented in combination with those described in connection with the first to third embodiments.

Having a simple structure, the sensor unit SU can be built compact; in particular, having a shape like a medal, the sensor unit SU can be adapted to wearable devices in various forms. That is, it is possible to build desired wearable devices incorporating the sensor unit SU. Building wearable devices by use of the sensor unit SU allows the sensor unit SU to be attached easily to desired spots on the human body. Such a wearable device can be grasped as being provided with an attachment member for keeping the sensor unit SU attached to the human body as a subject. The measurement device (see FIG. 7A, etc.) discussed in connection with the second embodiment is a kind of wearable device, and the attachment band 4 corresponds to the attachment member. The attachment member is not limited to an attachment band 4, but may be anything that permits the sensor unit SU to be attached to the human body as a subject.

Attachment to the human body may be direct. In that case, attachment to the human body brings direct contact of the sensor unit SU with the formative tissue (typically, the skin) of the human body. Attachment to the human body may instead be indirect. In indirect attachment, the sensor unit SU is fitted to the clothes worn around the human body or the belt or the like worn around the waist of the human body so that, via the clothes or the belt or the like, the sensor unit SU is attached to the human body, in which case no direct contact of the sensor unit SU with the formative tissue (typically, the skin) of the human body results.

FIGS. 21A to 21D are exterior views of wearable devices WD1 to WD4 as examples of wearable devices configured to incorporate the sensor unit SU.

Like the measurement device (see FIG. 7A, etc.) discussed in connection with the second embodiment, the wearable device WD1 is a wrist watch-type wearable device, and includes the sensor unit SU and an attachment band which is coupled to the sensor unit SU and which permits the sensor unit SU to be attached to a user's wrist. The wearable device WD1 may include a display screen for displaying the current time acquired by use of the timer 40 of the sensor unit SU (the same applies to the wearable devices WD2 to WD4).

The wearable device WD2 is a wrist band-type wearable device, and includes the sensor unit SU and an attachment band which is coupled to the sensor unit SU and which permits the sensor unit SU to be attached to a user's wrist.

The wearable device WD3 is a necklace-type wearable device, and includes the sensor unit SU and a ring member in the shape of a ring which is coupled to the sensor unit SU and which permits the sensor unit SU to be hung from a user's neck. When the user wears the wearable device WD3, the sensor unit SU is located at the position of the pendant top of the necklace.

The wearable device WD4 is a badge-type wearable device, and includes the sensor unit SU and a clip member which is coupled to the sensor unit SU and which permits the sensor unit SU to be fitted to the user's clothes or a belt or the like worn around the user's waist.

As described above, the sensor unit SU is configured to be capable of acquiring orientation information. Orientation information is considered particularly apt for wearable devices, and combining orientation information with step count information (the number of steps counted by the pedometer function) makes it possible to determine the direction and distance of the movement of a user wearing a wearable device. For example, by putting a wearable device including the sensor unit SU on a subject to be watched, and transferring information indicating the direction and distance of the movement of the subject being watched from the sensor unit SU to the terminal device TM, it is possible to realize watching support. In the future, the terminal device TM can be additionally provided with a function for indoor navigation, where location identification by a GPS (global positioning system) is difficult, thereby to achieve enhanced watching support.

All or part of the above-mentioned information calculated or derived by the microcomputer 20 may be calculated or derived on the part of the terminal device TM. That is, all or part of the functions of the microcomputer 20 may be performed by a microcomputer provided in the terminal device TM.

The sensor unit SU itself or part of the components of the sensor unit SU (for example, the component group 1) may be incorporated in a mobile device. Examples of mobile devices include information terminals, mobile telephones, and personal computers. So-called smartphones belong to information terminals, mobile telephones, or personal computers. In that case, when indices $P_1$ to $P_3$ are derived, for example, the evaluation movement can be performed with the mobile device held in the palm such that the mobile device is kept in a fixed position before the chest. The terminal device TM described above can be considered a kind of mobile device, and wearable devices too can be considered a kind of mobile device. A mobile device includes a display screen which can display any information, a communication unit which can communicate with another information device via a network such as the Internet, an audio output unit which comprises a loudspeaker and the like that can output audio, a telephony unit which achieves speech communication with a partner device, and the like. A mobile device is often provided with an acceleration sensor for sensing the inclination or the like of the mobile device, in which case the acceleration sensor for sensing the inclination or the like of the mobile device may be used to double as the acceleration sensor 11. The processing to be performed by the microcomputer 20 can then be performed by the microcomputer provided in the mobile device.

As described above, the sensor unit SU has, in addition to a function of measuring the amount of activity, a function of measuring the muscular power (a function of deriving a muscular power index). Thus, the sensor unit SU allows life-logging as to physical activities such as walking and running (management of the history of amounts of activity), and can estimate the muscular power condition from a person's movements. The sensor unit SU thus contributes to the management of a person's health condition. That is, it is possible to measure an index related to muscular power more easily than by other methods like that disclosed in Non-Patent Document 1, and by quantifying muscular power, it is possible to promote the visualizing of deterioration of muscular power due to a lack of physical exercise or due to aging, and to control health on higher levels such as by preventing injuries due to deterioration of muscular power, preventing confinement to bed, administering presymptomatic measures, and motivating to rehabilitation.

Having the function of deriving an activity efficiency index, the sensor unit SU can evaluate whether or not a physical activity performed is efficient. If it is found inefficient, it is then possible to change the regimen of physical activities for the future.

<Study on the Present Invention>>

To follow is a study on the present invention described above.

According to one aspect of the present invention, an index deriving device (SU) which includes an acceleration sensor (11) for sensing acceleration and which can derive the amount of activity of a human body includes: a muscular power index deriver (20) configured to derive a muscular power index (for example, $P_1$ or $P_3$) as to the muscular power of the human body based on the sensing result from the acceleration sensor; and a separate index deriver (20) configured to derive a separate index commensurate with the variation of the muscular power index against the amount of activity during a predetermined activity monitoring period.

It is thus possible to derive, as a separate index, the relationship between the amount of activity and the muscular power index; for example, it is possible to evaluate whether or not a physical activity performed is efficient. If it is found inefficient, it is then possible to change the regimen of physical activities for the future. That is, it is possible to know easily the quality of physical activities, which it is impossible to know with conventional devices.

In the embodiments described above, the microcomputer 20 can be grasped as including an activity amount deriver which derives the amount of activity, a muscular power index deriver which derives a muscular power index, and a separate index deriver (activity efficiency index deriver) which derives, as a separate index, an activity efficiency index.

A target device according to the present invention (index deriving device, wearable device, or a mobile device) can be built as hardware, such as an integrated circuit, or as a combination of hardware and software. Arbitrary particular functions, which are all or part of the functions performable by the target device, may be written in a program, and this program may be stored in a flash memory that can be mounted on the target device so that, when the program is run on a program execution device (for example, a microcomputer that can be mounted on the target device), those particular functions will be performed. The program can be stored in or fixed to any recording medium. The recording medium in or to which the program is stored or fixed may be mounted on or connected to a device (such as a server device) separate from the target device.

LIST OF REFERENCE SIGNS

SU sensor unit
TM terminal device
1 component group
2 circuit board
3 housing
10 sensor arrangement
11 acceleration sensor
12 atmospheric pressure sensor
13 orientation sensor
20 microcomputer
30 memory
40 timer
50 wireless processor

The invention claimed is:

1. An index deriving device which includes an acceleration sensor for sensing acceleration and which can derive an amount of activity of a human body, the amount of activity being a quantity commensurate with a duration of physical exertion multiplied by an intensity of physical exertion with respect to a physical activity of the human body during a predetermined activity monitoring period, the index deriving device comprising:
  a muscular power index deriver configured to derive, separately from the amount of activity, a muscular power index as to muscular power of the human body based on a sensing result from the acceleration sensor; and
  a separate index deriver configured to derive a separate index, wherein the separate index deriver is configured to derive the separate index based on:
    a muscular power index derived before the activity monitoring period,
    the amount of activity during the activity monitoring period, and
    a muscular power index derived after the activity monitoring period,
  wherein
  the muscular power index deriver is configured to derive the muscular power index based on an acceleration signal based on the sensing result from the acceleration sensor during an evaluation period in which the human body performs a predetermined movement,
  the muscular power index deriver is configured to derive the muscular power index by using acceleration maximum value data contained in the acceleration signal, and
  the muscular power index deriver is configured to derive the muscular power index by using:
    the acceleration maximum value data, a body weight of the human body, and a body fat percentage of the human body;
    the acceleration maximum value data, the body weight of the human body, and a body fat mass of the human body;

the acceleration maximum value data, the body weight of the human body, and a muscle percentage of the human body; or the acceleration maximum value data and a muscle mass of the human body.

2. The index deriving device according to claim 1, wherein the separate index deriver derives the separate index by dividing a difference between the muscular power index derived before the activity monitoring period and the muscular power index derived after the activity monitoring period by the amount of activity during the activity monitoring period.

3. The index deriving device according to claim 1, wherein the muscular power index deriver derives, as the muscular power index, an acceleration maximum value per unit amount of muscle of the human body in the predetermined movement.

4. The index deriving device according to claim 1, wherein
the acceleration sensed by the acceleration sensor contains an acceleration component due to the movement of the human body and an acceleration component due to gravity, and
the muscular power index deriver derives the muscular power index by using a value obtained by subtracting the acceleration component due to gravity from the acceleration maximum value data.

5. The index deriving device according to claim 1, wherein
acceleration along three mutually perpendicular axes individually, and
the acceleration signal used to derive the muscular power index represents a magnitude of an acceleration vector formed by the acceleration along the three axes.

6. The index deriving device according to claim 1, wherein the predetermined movement includes a movement in which the human body stands up.

7. The index deriving device according to claim 1, further comprising:
an atmospheric pressure sensor for sensing atmospheric pressure, and
the amount of activity is derived based on
the sensing result from the acceleration sensor and
a sensing result from the atmospheric pressure sensor.

8. The index deriving device according to claim 1, comprising:
a circuit board which has mounted thereon:
a sensor arrangement including the acceleration sensor;
a calculation processor configured to derive the amount of activity, the calculation processor constituting the muscular power index deriver and the separate index deriver; and
a wireless processor configured to conduct wireless communication; and
a housing which houses the circuit board.

9. A wearable device comprising the index deriving device according to claim 1.

10. A mobile device comprising the index deriving device according to claim 1.

* * * * *